United States Patent [19]

Binder et al.

[11] Patent Number: 4,927,821
[45] Date of Patent: May 22, 1990

[54] ENOL ETHERS OF 6-CHLORO-4-HYDROXY-2-METHYL-N-(2-PYRIDYL)-2H-THIENO(2,3-E)-1,2-THIAZINE-3-CARBOXAMIDE 1,1-DIOXIDE, AND THEIR USE

[75] Inventors: Dieter Binder, Vienna; Franz Rovenszky, Bruck a.d. Leitha; Hubert P. Ferber, Ansfelden, all of Austria

[73] Assignee: CL Pharma Aktiengesellschaft, Linz, Austria

[21] Appl. No.: 262,499

[22] Filed: Oct. 18, 1988

[30] Foreign Application Priority Data

Oct. 29, 1987 [AT] Austria ................. 2855/87

[51] Int. Cl.$^5$ ............... A61K 31/54; C07D 513/04
[52] U.S. Cl. ...................... 514/226.5; 544/48
[58] Field of Search ................. 514/226.5; 544/48

[56] References Cited

U.S. PATENT DOCUMENTS 4,180,662 12/1979 Pfister et al. ................. 544/48
4,551,452 11/1985 Marfat ......................... 514/222

FOREIGN PATENT DOCUMENTS 147177 10/1987 European Pat. Off. .

Primary Examiner—John M. Ford
Attorney, Agent, or Firm—Wenderoth, Lind & Ponack

[57] ABSTRACT

The invention relates to new enol ethers of 6-chloro-4-hydroxy-2-methyl-N-(2-pyridyl)-2H-thieno(2,3-e)-1,2-thiazine-3-carboxamide 1,1-dioxide of the formula

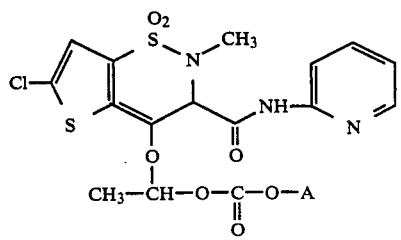

in which R denotes $(C_1-C_6)$-alkyl, $(C_5-C_7)$-cycloalkyl or benzyl, and a process for their preparation. The new compounds have an antiinflammatory activity and are suitable for the treatment of rheumatism.

4 Claims, No Drawings

ENOL ETHERS OF 6-CHLORO-4-HYDROXY-2-METHYL-N-(2-PYRIDYL)-2H-THIENO(2,3-E)-1,2-THIAZINE-3-CARBOXAMIDE 1,1-DIOXIDE, AND THEIR USE

The invention relates to new enol ethers of 6-chloro-4-hydroxy-2-methyl-N-(2-pyridyl)-2H-thieno(2,3-e)-1,2-thiazine-3-carboxamide 1,1-dioxide, a process for their preparation and their use in medicaments with an antiinflammatory action.

Antiinflammatory analgesics are described in U.S. Patent Specification 4,180,662. Of the substances described in this U.S. Patent Specification, 6-chloro-4-hydroxy-2-methyl-N-(2-pyridyl)-2H-thieno(2,3-e)-1,2-thiazine-3-carboxamide 1,1-dioxide (chlortenoxicam) has proved to be particularly effective. However, because of its polar and acidic structure, this compound can in rare cases cause irritation of the gastrointestinal tract. Topical formulations of this substance have the disadvantage that they can penetrate the skin only unsatisfactorily and their intense yellow colour stains items of clothing covering them.

Oxicam enol ethers are known from European Patent Specification 0,147,177. The enol ethers described in this European Patent Specification have the disadvantage, however, that the pharmacological activity of these enol ethers is lower than the activity of the non-etherified oxicams.

Surprisingly, it has now been found that the enol ethers of the present invention, which are colourless and are therefore also suitable for topical applications, have a higher pharmacological activity than the non-etherified chlortenoxicam.

The invention therefore relates to compounds of the formula I

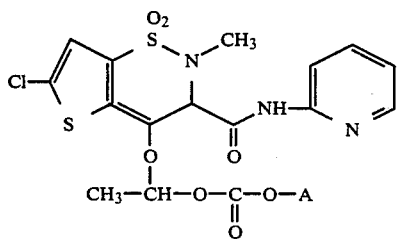

in which R denotes $(C_1-C_6)$-alkyl, $(C_5-C_7)$-cycloalkyl or benzyl.

The term $(C_1-C_6)$-alkyl used in this description describes straight-chain or branched saturated hydrocarbon radicals with 1-6 carbon atoms, such as, for example, methyl, ethyl, isopropyl, tert.-butyl and hexyl. Halogen is to be understood as chlorine, bromine or iodine.

A preferred individual compound is: 6-chloro-4-(1-(ethoxycarbonyloxy)ethoxy)-2-methyl-N-(2-pyridyl)-2H-thieno(2,3-e)-1,2-thiazine-3-carboxamide 1,1-dioxide.

The compounds of the formula I are prepared by a process in which a salt of chlortenoxicam of the formula II

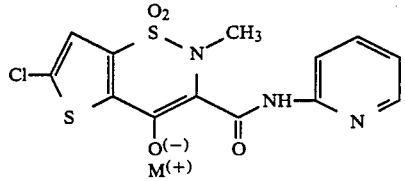

in which M+ denotes an alkali metal cation or alkaline earth metal cation or tetraalkylammonium, is reacted with a compound of the formula III

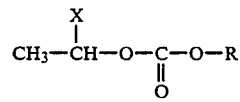

in which R has the above meaning and X denotes halogen, in a polar aprotic solvent which is inert towards the reaction.

The required salts of chlortenoxicam can be used in the isolated form; preferably, however, they are produced in situ by addition of at least one equivalent of a strong base, such as, for example, alkali metal hydrides or alkali metal carbonates, in a polar, aprotic, anhydrous solvent which is inert towards the reaction, such as, for example, dimethylformamide, dimethyl sulphoxide, acetone, 2-butanone and the like. The reaction temperature is not critical and is between room temperature and the boiling point of the particular solvent used.

The reaction time depends on the reaction temperature and the leaving group X; it is in general between 2 and 30 hours. The reaction can be accelerated by addition of sodium iodide (Finckelstein reaction), NaI being employed in a 0.5-threefold excess based on the alkylating agent. Preferred reaction conditions are the reaction of chlortenoxicam with compounds of the formula III in acetone as the solvent and sodium carbonate or potassium carbonate as the base in excess at reflux temperature and an approximately 1.5-fold excess of NaI, based on the alkylating agent.

Chlortenoxicam can be prepared in accordance with U.S. Patent Specification 4,180,662. The compounds of the formula III are either commercially available or can be prepared in accordance with the method of H. Müller, J. Liebigs Ann. Chem. 258, 50 (1890) or in accordance with European Patent Specification 0,147,177.

The new compounds of the formula I exhibit an outstanding antiinflammatory activity in in vitro models.

On the basis of this pharmacological property, the new compounds can be used by themselves or as a mixture with other active substances in the form of customary galenical formulations for inhibiting inflammation and combating pain in diseases such as rheumatism.

The antiinflammatory property can be determined by means of generally known standard methods, such as, for example, the carrageenan-induced rat paw swelling test. In this test (Example 2), in which chlortenoxicam, an enol ether of chlortenoxicam, that is to say 6-chloro-4-(1-(ethoxycarbonyloxy)ethoxy)-2-methyl-N-(2-pyridyl)-2H-thieno(2,3-e)-1,2-thiazine-3-carboxamide 1,1-dioxide, piroxicam (2-methyl-N-(2-pyridyl)-4-hydroxy-2H-1,2-benzothiazine-3-carboxamide 1,2-dioxide) and an enol ether of piroxicam, that is to say 4-(1-ethoxycarbonyloxy)ethoxy)-2-methyl-N-(2-pyridyl)-

2H-1,2-benzothiazine-3-carboxamide 1,1-dioxide, were compared in their antiinflammatory activity, it was found that under the given experimental conditions 80% inhibition of inflammation was to be achieved only with the enol ether of chlortenoxicam. From the values for the 50% inhibition of inflammation, it can be deduced that the enol ether of chlortenoxicam is almost twice as effective as chlortenoxicam, whereas the enol ether of piroxicam is considerably less effective than piroxicam. The following sequence of decreasing antiinflammatory potency thus results: chlortenoxicam enol ether/chlortenoxicam/piroxicam/piroxicam enol ether The compounds of the formula I are intended for use on mammals, in particular on humans, and can be administered in the customary manner, such as, for example, orally or parenterally. They are preferably administered orally or topically, the daily dose for oral administration being about 0.5 to 100 mg, preferably 1.0 to 10 mg. However, the treating physician can also prescribe doses above or below this, depending on the general condition and age of the patient, the appropriate substance of the formula I, the nature of the disease and the nature of the formulation. In the case of topical application, the concentration of the compound of the formula I is between 0.01 and 3%.

The compounds of the formula I can be administered by themselves or in combination with other pharmaceutically active substances, the content of the compounds of the formula I being between 0.1 and 99%. The pharmaceutically active compounds are in general present as a mixture with suitable inert auxiliaries and/or excipients or diluents, such as, for example, pharmaceutically acceptable solvents, gelatine, gum arabic, lactose, starch, magnesium stearate, talc, vegetable oils, polyalkylene glycol, petroleum jelly and the like.

The pharmaceutical preparations can be in solid form, for example as tablets, coated tablets, suppositories, capsules and the like, in semi-solid form, for example as ointments or gel, or in liquid form, for example as solutions, suspensions or emulsions. If appropriate, they are sterilized and contain auxiliaries, such as preservatives, stabilizers, emulsifying agents, salts for modifying the osmotic pressure and the like.

In particular, pharmaceutical preparations can contain the compounds according to the invention in combination with other therapeutically useful substances. The compounds according to the invention can be formulated to combination preparations with these, for example together with the abovementioned auxiliaries and/or excipients or diluents.

EXAMPLE 1:

6-Chloro-4-(1-(ethoxycarbonyloxy)ethoxy)-2-methyl-N-(2-pyridyl)-2H-thieno(2,3-e)-1,2-thiazine-3-carboxamide 1,1-dioxide 10 g (26.9 mmol) of 6-chloro-4-hydroxy-2-methyl-N-(2-pyridyl)-2H-thieno-(2,3-e)-1,2-thiazine-3-carboxamide 1,1-dioxide, 9.29 g (99.5 mmol) of potassium carbonate and 15.1 g (99.5 mmol) of 1-chloroethyl ethyl carbonate are heated under reflux in 150 ml of acetone for 20 hours. 24.5 g (163.3 mmol) of sodium iodide are then added and the mixture is heated under reflux for a further 5 hours. Thereafter, the sodium chloride which has precipitated out is filtered off with suction, the filtrate is evaporated and the residue is partitioned between 100 ml of methylene chloride and 100 ml of saturated sodium bicarbonate solution. The phases are separated and the organic phase is washed with 100 ml of water and 20 ml of 3% strength sodium bisulphite solution. The organic phase is dried over sodium sulphate, filtered and evaporated. The resulting oily crude product (17.5 g) is filtered over silica gel (100 g of silica gel 60, particle size 0.04–0.063 mm, eluent: methylene chloride:ethyl acetate=9:1). 10.1 g of pale orange crystals are obtained. These are dissolved in 17 ml of dioxane at the boiling point, 0.6 g of active charcoal is added to the solution and the solution is then filtered hot. The filtrate is cooled and 40 ml of diethyl ether are added. The colourless crystals which have precipitated out are filtered off with suction, washed with ether and dried at 50° C./1 mbar.

Yield: 6.3 g of colourless crystals (48% of theory)
Melting point: 148° C. (decomposition)
$^1$H-NMR (CDCl$_3$):

delta (ppm): 8.9 (s broad; 1H; —NH—); 8.3 (m; 2H; Py—H); 7.8 (m; 1H; Py—H); 7.2 (s; 1H; Th—H); 7.1 (m; 1H; Py—H); 6.5 (q; 1H; O—CH—O); 4.1 (q; 2H; —CH$_2$—); 3.2 (s; 3H; N—CH$_3$); 1.7 (d; 3H; —CH—CH$_3$); 1.2 (t; 3H; —CH$_2$—CH$_3$). $^{13}$C-NMR (CDCl$_3$):

delta (ppm): 157.9; 153.1; 150.5; 147.9; 142.1; 137.9; 135.9; 135.5; 134.9; 126.6; 121.1; 120.1; 113.9; 100.1; 64.4; 36.7; 19.9; 13.7.

EXAMPLE 2

Carrageenan-induced rat paw swelling test

The antiinflammatory action of the test substances was tested by their inhibitory action on carrageenan-induced swelling of the raw paw.

The test substances used were:
chlortenoxicam (6-chloro-4-hydroxy-2-methyl-N-(2-pyridyl)-2H-thieno(2,3-e)-1,2-thiazine-3-carboxamide 1,1-dioxide)
chlortenoxicam enol ether (6-chloro-4-(1-(ethoxycarbonyloxy)ethoxy)-2-methyl-N-(2-pyridyl)-2H-thieno(2,3-e)-1,2-thiazine-3-carboxamide 1,1-dioxide)
piroxicam (2-methyl-N-(2-pyridyl)-4-hydroxy-2H-1,2-benzothiazine-3-carboxamide 1,1-dioxide)
piroxicam enol ether (4-(1-(ethoxycarbonyloxy)ethoxy)-2-methyl-N-(2-pyridyl)-2H-1,2-benzothiazine-3-carboxamide 1,1-dioxide)

Before the start of the experiment, the volume of the right-hand hind paw of the raw was determined by plethysmometry and recorded in ml of water displaced.

The test substances were administered orally by means of a stomach tube as a suspension in 0.5% strength carboxymethylcellulose. The dosage was 0.3/1.0/3.0 and 10 mg/kg of body weight. 8 animals were tested per substance and dose or control. After one hour, inflammation was induced by injection of 0.05 ml of a 2% strength solution of lambda carrageenan in 0.9% NaCl into the right hind paw of the experimental animals. 3 and 4 hours after inflammation had been induced, the volume of the right-hand hind paw of the raw was again determined by plethysmometry. The inhibitory of inflammation is stated in %. The 80% and 50% IHD (inhibitory dose) are calculated from these values. (The 80% IHD indicates that dose in mg/kg of body weight which is capable of inhibiting inflammation to the extent of 80%).

80% IHD values:

| Substance | 3 hours after carrageenan (mg/kg) | 4 hours after carrageenan (mg/kg) | geometric mean (mg/kg) |
|---|---|---|---|
| chlortenoxicam enol ether | 3.01 | 3.03 | 3.02 |
| chlortenoxicam | n.r. | n.r. | n.r. |
| piroxicam | n.r. | n.r. | n.r. |
| piroxicam enol ether | n.r. | n.r. | n.r. | n.r.: not reached

50% IHD values:

| Substance | 3 hours after carrageenan (mg/kg) | 4 hours after carrageenan (mg/kg) | geometric mean (mg/kg) |
|---|---|---|---|
| chlortenoxicam enol ether | 0.23 | 0.36 | 0.29 |
| chlortenoxicam | 0.35 | 0.60 | 0.46 |
| piroxicam | 3.88 | 5.06 | 4.43 |
| piroxicam enol ether | g.t. 10 | g.t. 10 | g.t. 10 | g.t.: greater than

EXAMPLE 3:

Preparation of a chlortenoxicam enol ether gel batch 8 g of 6-chloro-4-(1-(ethoxycarbonyloxy)ethoxy)-2-methyl-N-(2-pyridyl)-2H-thieno(2,3-e)-1,2-thiazine-3-carboxamide 1,1-dioxide are dissolved in 4,717 g of ethanol and 2,082 g of water in a FRYMA process plant. 167 g of Carbopol are introduced into this solution, in portions, with stirring. After addition of 139 g of Luvitol EHO, the batch is neutralized with a solution prepared from 83 g of diisopropylamine, 833 g of ethanol and 833 g of water and then brought to a pH of 7.5 with a solution consisting of 28 g of diisopropylamine, 555 g of ethanol and 555 g of water. Tubes are filled with the gel.

What we claim is:

1. A compound of the formula

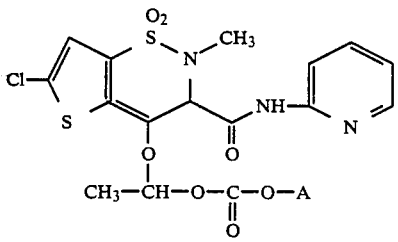

in which R denotes $(C_1-C_6)$-alkyl, $(C_5-C_7)$-cycloalkyl or benzyl.

2. 6-Chloro-4-(1-(ethoxycarbonyloxy)ethoxy)-2-methyl-N-(2-pyridyl)-2H-thieno-(2,3-e)-1,2-thiazine-3-carboxamide 1,1-dioxide.

3. A pharmaceutical composition containing a compound of formula I as claimed in claim 1 in an amount effective for the treatment of inflammatory diseases in combination with pharmaceutically acceptable excipients, carrier or diluents.

4. A method for the treatment of inflammatory diseases, which comprises administering to a patient an effective amount of a compound of formula I as claimed in claim 1 in combination with pharmaceutically acceptable excipients, carrier or diluents.

* * * * *